(12) United States Patent
Hart

(10) Patent No.: US 9,096,896 B2
(45) Date of Patent: Aug. 4, 2015

(54) METHOD FOR QUANTIFYING DNA IN A BIOLOGICAL SAMPLE

(75) Inventor: Hope Hart, Durham, NC (US)

(73) Assignee: Syngenta Participations AG, Basel (CH)

( * ) Notice: Subject to any disclaimer, the term of this patent is extended or adjusted under 35 U.S.C. 154(b) by 223 days.

(21) Appl. No.: 13/378,869

(22) PCT Filed: Jun. 18, 2010

(86) PCT No.: PCT/US2010/039109
§ 371 (c)(1),
(2), (4) Date: Jan. 12, 2012

(87) PCT Pub. No.: WO2010/148268
PCT Pub. Date: Dec. 23, 2010

(65) Prior Publication Data
US 2012/0100544 A1    Apr. 26, 2012

Related U.S. Application Data

(60) Provisional application No. 61/218,155, filed on Jun. 18, 2009.

(51) Int. Cl.
C12Q 1/68      (2006.01)
C12P 19/34     (2006.01)
C07H 21/04     (2006.01)

(52) U.S. Cl.
CPC ................................. *C12Q 1/6851* (2013.01)

(58) Field of Classification Search
USPC ............... 435/91.2, 6.12; 536/24.32, 22.1
See application file for complete search history.

(56) References Cited

U.S. PATENT DOCUMENTS

| 7,129,041 B2 * | 10/2006 | Merigan et al. ............... 435/5 |
| 7,635,799 B2 * | 12/2009 | Johnson et al. ............ 800/284 |
| 2002/0133845 A1 | 9/2002 | Michiels et al. |
| 2008/0034453 A1 | 2/2008 | Cheikh et al. |

FOREIGN PATENT DOCUMENTS

| CN | 1584049 A | 2/2005 |
| EP | 1724360 A1 | 11/2006 |
| WO | WO 2007/019532 A2 | 2/2007 |

OTHER PUBLICATIONS

Lowe et al. (Nucleic Acid Research, 1990, vol. 18(7), p. 1757-1761.*
Nucleic acid sequence search repports AC: AY123624 (2002), AED49963 (2005) and GV611453(2010).*
Hernandez et al. "Development and Comparison of Four Real-Time Polymerase Chain Reaction Systems for Specific Detection and Quantification of *Zea mays* L." *J. Agric. Food Chem.* 52:4632-4637 (2004).
Ronning et al. "Event specific real-time quantitative PCR for genetically modified Bt11 maize (*Zea mays*)", *Eur Food Res Technol* 216:347-354 (2003).
"Performance Assessment Bt11 Maize PCR Assay", *Eurofins GeneScan* pp. 1-3 (2007).
"Event-specific Method for the Quantification of Maize Event Bt11 Using Real-time PCR: Validation Report", *Joint Research Centre Institute for Health and Consumer Protection Biotechnology & GMOsUnit* pp. 1-16 (2008).
"Event-specific Method for the Quantification of Maize Line Bt11 Using Real-time PCR: Protocol", *Joint Research Centre Institute for Health and Consumer Protection Biotechnology & GMOs Unit* pp. 1-10 (2008).
International Search Report corresponding to PCT/US2010/039109 mailed Aug. 30, 2010.
Written Opinion corresponding to PCT/US2010/039109 mailed Aug. 30, 2010.
European Search Report corresponding to European Application No. 10790234.8 dated Oct. 11, 2012.
Notification Concerning Transmittal of International Preliminary Report on Patentability and Written Opinion of the International Searching Authority corresponding to PCT/US2010/039109 mailed Jan. 5, 2012.

* cited by examiner

*Primary Examiner* — Kenneth R. Horlick
*Assistant Examiner* — Joyce Tung
(74) *Attorney, Agent, or Firm* — Yoshimi D. Barron

(57) ABSTRACT

Improved methods of quantifying nucleic acids that are unique to a transgenic corn event designated Bt11 in a biological sample and compositions thereof are disclosed. The invention further relates to primer pairs used in the method that are unique to event Bt11.

7 Claims, No Drawings

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Bt11-ev-f1 forward Bt11 primer

<400> SEQUENCE: 1
tgtgtggcca tttatcatcg a                                          21

<210> SEQ ID NO 2
<211> LENGTH: 21
<212> TYPE: DNA
<213> ORGANISM: Artificial Sequence
<220> FEATURE:
<223> OTHER INFORMATION: Bt11-ev-r5 Bt11 reverse primer

<400> SEQUENCE: 2
cgctcagtgg aacgaaaact c                                          21

<210> SEQ ID NO 3
<211> LENGTH: 29
<212> TYPE: DNA
<213> ORGANISM: Artificial Sequence
<220> FEATURE:
<223> OTHER INFORMATION: Bt11-ev-p1 Bt11 probe

<400> SEQUENCE: 3
ttccatgacc aaaatccctt aacgtgagt                                  29

<210> SEQ ID NO 4
<211> LENGTH: 68
<212> TYPE: DNA
<213> ORGANISM: Artificial Sequence
<220> FEATURE:
<223> OTHER INFORMATION: Bt11 5' amplicon

<400> SEQUENCE: 4
tgtgtggcca tttatcatcg acttccatga ccaaaatccc ttaacgtgag ctttcgttcc    60
actgagcg                                                          68

<210> SEQ ID NO 5
<211> LENGTH: 21
<212> TYPE: DNA
<213> ORGANISM: Artificial Sequence
<220> FEATURE:
<223> OTHER INFORMATION: ZmAdh1-F forward primer

<400> SEQUENCE: 5
cgtcgtttcc catctcttcc t                                          21

<210> SEQ ID NO 6
<211> LENGTH: 20
<212> TYPE: DNA
<213> ORGANISM: Artificial Sequence
<220> FEATURE:
<223> OTHER INFORMATION: Zmadh1-R reverse primer
```

```
<400> SEQUENCE: 6
ccactccgag accctcagtc                                                           20

<210> SEQ ID NO 7
<211> LENGTH: 27
<212> TYPE: DNA
<213> ORGANISM: Artificial Sequence
<220> FEATURE:
<223> OTHER INFORMATION: ZmAdh1-P probe

<400> SEQUENCE: 7
aatcagggct cattttctcg ctcctca                                                   27

<210> SEQ ID NO 8
<211> LENGTH: 134
<212> TYPE: DNA
<213> ORGANISM: Artificial Sequence
<220> FEATURE:
<223> OTHER INFORMATION: Adh1 amplicon

<400> SEQUENCE: 8
cgtcgtttcc catctcttcc tcctttagag ctaccactat ataaatcagg gctcattttc               60 tgctcctca caggctcatc tcgctttgga tcgattggtt tcgtaagtgg tgagggactg              120
agggtctgga gtgg                                                               134
```

METHOD FOR QUANTIFYING DNA IN A BIOLOGICAL SAMPLE

STATEMENT OF PRIORITY

This application is a 35 U.S.C. §371 national stage application of PCT Application No. PCT/US2010/039109, filed on Jun. 18, 2010, which claims priority from U.S. Provisional Application No. 61/218,155, filed on Jun. 18, 2009, the entire contents of which are incorporated by reference herein. The above-referenced PCT International Application was published as International Publication No. WO 2010/148268 A1 on Dec. 23, 2010.

BACKGROUND

The present invention relates to improved methods of quantifying nucleic acids that are unique to a transgenic corn event designated Bt11 in a biological sample and to compositions useful in performing the methods.

Consequential to the implementation of regulations surrounding transgenic crop plants, for example European Commission (EC) Regulation 1139/98, EC Regulation 49/2000, and EC Regulation 50/2000, there has been the need to measure accurately the levels of DNA from a transgenic species that may be present: in for example, grain used for food. Analytical methods to detect and quantify DNA from these transgenic plants have received much attention particularly because the threshold value for labeling, set down by the European Commission's Standing Committee in 1999, is 1%.

It is possible to detect the presence of a transgene by any well-known nucleic acid detection method including but not limited to thermal amplification (polymerase chain reaction (PCR)) using polynucleotide primers or DNA hybridization using nucleic acid probes. Typically, for the sake of simplicity and uniformity of reagents and methodologies for use in detecting a particular DNA construct that has been used for transforming various plant varieties, these detection methods generally focus on frequently used genetic elements, for example, promoters, terminators, and marker genes, because for many DNA constructs, the coding sequence region is interchangeable. As a result, such methods may not be useful for discriminating between constructs that differ only with reference to the coding sequence. In addition, such methods may not be useful for discriminating between different transgenic events, particularly those produced using the same DNA construct.

To distinguish between transgenic events, event-specific PCR methods have been developed, insertion of a heterologous DNA construct into a plant's genome creates unique event-specific junctions between the integrated DNA sequence and the plant's genomic sequence. Event-specific quantitative PCR (qPCR) methods have been developed for transgenic events, including one for Bt11 Factors that may limit the applicability for such methods may include, for example, influences of initial DNA concentration, standards set by regulatory agencies, selection of primers and PCR protocol, repeatability from sample to sample, reproducibility between different laboratories, and thresholds for low level detection and high sensitivity.

For the foregoing reasons, there is a need for improving the quantitative detection of nucleic acids from the Bt11 transgenic corn event in a biological sample.

SUMMARY

The present invention relates to a transformed corn (Zea may) event, designated Bt11 comprising two heterologous expression cassettes, one comprising a cry1Ab coding sequence that encodes a Cry1Ab insecticidal protein that confers insect resistance to Bt11 corn plants and the other comprising a pat coding sequence encoding a PAT protein that confers upon Bt11 corn plants resistance to glufosinate-ammonium herbicides. The creation of the Bt11 event is described in U.S. Pat. No. 6,114,608, the contents of which are hereby incorporated by reference. The two expression cassettes where inserted within a 15 cM region on the long arm of chromosome 8, near position 117, and in the interval flanked by two public markers: Z1B3 and UMC150a.

The present invention provides compositions and improved methods for the quantitative detection of B11-specific. DNA in biological samples relative to an endogenous maize adh1 gene. Such quantification of Bt11 DNA in, for example a mixture of corn grain comprising Bt11 and non-Bt11 grain, is based on a primer pair and probe designed to detect the 5 junction sequence in Bt11.

In one aspect of the present invention, a method for quantifying event Bt11 DNA in a biological sample comprising corn nucleic acids is provided wherein the method comprises (a) contacting the biological sample with a first pair of primers, comprising a first primer consisting of SEQ ID NO: 1 and a second primer consisting of SEQ ID NO; 2, and a fluorescent dye labeled probe comprising SEQ ID NO: 3, wherein the first pair of primers, when used in a nucleic-acid amplification reaction with genomic DNA from event Bt11 corn, produce a first amplicon comprising SEQ ID NO: 4, and wherein the first amplicon is diagnostic for event Bt11; (b) contacting the biological sample with a second pair of primers, comprising a first primer consisting of SEQ ID NO: 5 and a second primer consisting of SEQ ID NO: 6, and a second fluorescent dye labeled probe comprising SEQ ID NO: 7, wherein the second pair of primers, when used in a nucleic-acid amplification reaction with corn genomic DNA, produce a second amplicon comprising SEQ ID NC): 8, and wherein the second amplicon is indicative of the presence of a maize adh1 gene; (c) providing a nucleic acid amplification reaction condition and a PCR instrument capable of performing a quantitative real-time PCR; (d) performing the quantitative real-time PCR using the primers and probes of (a) and (b), thereby producing the first amplicon and the second amplicon; (e) detecting simultaneously the first amplicon and the second amplicon as they are produced by said PCR instrument; and (f) calculating a relative amount of the first amplicon compared to the second amplicon, whereby the amount of the first amplicon is indicative of the quantity of Bt11 DNA in the biological sample.

In another aspect, the present invention provides a pair of primers comprising a first primer consisting of SEQ ID NO: 1 and a second primer consisting of SEQ ID NO: 2, wherein the pair of primers, when used in a PCR with genomic DNA from event Bt11 corn, produce an amplicon comprising SEQ ID NO: 4 that is diagnostic for event Bt11.

In yet another aspect, the present invention provides a polynucleotide probe consisting of SEQ ID NO: 3 that when labeled with a fluorescent dye at the 5' and 3' ends is useful in a RT-qPCR for detection and quantification of the Bt11 amplicon.

The foregoing and other aspects of the invention will become more apparent from the following detailed description.

DESCRIPTION OF THE SEQUENCES IN THE SEQUENCE LISTING

SEQ ID NO: 1 is the Bt11-5For Primer.
SEQ ID NO: 2 is the Bt11-5Rev Primer.

SEQ ID NO: 3 is the Bt11 probe.
SEQ ID NO: 4 is the Bt11 qPCR amplicon.
SEQ ID NO: 5 is the Zmadh1-F Primer.
SEQ ID NO: 6 is the Zmadh1-R Primer.
SEQ ID NO: 7 is the Zmadh1-P Probe.
SEQ ID NO: 8 is the adh1 qPCR amplicon.

DETAILED DESCRIPTION

The following definitions are provided to better define the present invention and to guide those of ordinary skill in the art in the practice of the present invention. Unless otherwise noted, terms used herein are to be understood according to conventional usage by those of ordinary skill in the relevant art. Definitions of common terms in molecular biology may also be found in Rieger et al., Glossary of Genetics: Classical and Molecular, 5$^{th}$ edition, Springer-Verlag: New York, 1994. The nomenclature for DNA bases and amino acids as set forth in 37 C.F.R. §1.822 is used herein.

"Accuracy" of a PCR method means the closeness of agreement between a test result and an accepted reference value.

"Amplification efficiency" means the rate of amplification that leads to a theoretical slope of –3.32 with an efficiency of 100% in each cycle. The efficiency of the reaction can be calculated by the following equation: Efficiency= $[10^{(-1/slope)}]-1$.

As used herein, the term "amplified" means the construction of multiple copies of a nucleic acid molecule or multiple copies complementary to the nucleic acid molecule using at least one of the nucleic acid molecules as a template. Amplification systems include, but not limited to the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

The "coefficient of linearity ($R^2$)" is the correlation coefficient of a standard curve obtained by linear regression analysis.

"Dynamic range" as used herein means the range of Bt11 DNA concentrations over which the method of the invention performs in a linear manner with an acceptable level of accuracy and precision.

As used herein the term transgenic "event" refers to a recombinant plant produced by transformation and regeneration of a plant cell or tissue with heterologous DNA, for example, an expression cassette that includes a gene of interest. The term "event" refers to the original transformant and/or progeny of the transformant that include the heterologous DNA. The term "event" also refers to progeny produced by a sexual outcross between the transformant and another corn line. Even after repeated backcrossing to a recurrent parent, the inserted DNA and the flanking DNA from the transformed parent is present in the progeny of the cross at the same chromosomal location. The term "event" also refers to DNA from the original transformant comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA. Normally, transformation of plant tissue produces multiple events, each of which represent insertion of a DNA construct into a different location in the genome of a plant cell. Based on the expression of the transgene or other desirable characteristics, a particular event is selected. Thus, "event Bt11", "Bt11" "Bt11 event" may be used interchangeably.

"Expression cassette" as used herein means a nucleic acid molecule capable of directing expression of a particular nucleotide sequence in an appropriate host cell, comprising a promoter operably linked to the nucleotide sequence of interest that is operably linked to termination signals. It also typically comprises sequences required for proper translation of the nucleotide sequence. The expression cassette may also comprise sequences not necessary in the direct expression of a nucleotide sequence of interest but which are present due to convenient restriction sites for removal of the cassette from an expression vector. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of die host cell by a transformation process known in the art. The expression of the nucleotide sequence the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development. An expression cassette, or fragment thereof, can also be referred to as "inserted sequence" or "insertion sequence" when transformed into a plant.

A "gene" is a defined region that is located within a genuine and that, besides a coding sequence, may comprise other, primarily regulatory, nucleic acid sequences responsible for the control of the expression, that is to say the transcription and translation, of the coding portion. A gene may also comprise other 5' and 3' untranslated sequences and termination sequences. Further elements that may be present are for example, introits.

A "heterologous" nucleic acid sequence is a nucleic acid sequence not naturally associated with a host cell into which it is introduced, including in naturally occurring multiple copies of a naturally occurring nucleic acid sequence.

"Limit of detection (LOD)" is the lowest amount or concentration of DNA in a sample, which can be reliably detected, but not necessarily quantified. The LOD of a method of the invention will be less than $\frac{1}{20}^{th}$ of the target concentration. Experimentally, a method of the invention will detect the presence of Bt11 DNA at least 95% of the time at the LOD, ensuring≤5% false negative results.

"Limit of quantitation (LOQ)" is the lowest amount or concentration of Bt11 DNA in a sample that can be reliably quantified with an acceptable level of precision and accuracy. The LOQ of a method of the invention will be less than $\frac{1}{10}^{th}$ of the value of the target concentration with an $RSD_r \leq 25\%$. Target concentration is intended as the threshold relevant thr legislative requirements.

"Practicability" means the ease of operation, the feasibility and efficiency of implementation, and/or the associated unitary costs (e.g. $/sample) of a method described herein.

"Primers" as used herein are isolated nucleic acids that are annealed to a complimentary target DNA strand by nucleic acid hybridization to form a hybrid between the primer and the target DNA strand, and then extended along the target DNA strand by a polymerase, such as DNA polymerase. Primer pairs or sets can be used for amplification of a nucleic acid molecule, for example, by the polymerase chain reaction (PCR) or other conventional nucleic-acid amplification methods.

A "probe" is an isolated nucleic acid to which is attached a conventional detectable label or reporter molecule, such as a chemiluminescent agent, radioactive isotope, ligand, or enzyme. Such a probe is complimentary to a strand of DNA from corn event Bt11 or a conventional corn line. The DNA of Bt11 can be from a Bt11 corn plant or from a sample that includes DNA from Bt11. Probes according to the present invention include not only deoxyribonucleic or ribonucleic acids but also polyamides and other probe materials that bind specifically to a target DNA sequence and can be used to detect the presence of that target DNA sequence.

Primers and probes are generally between 10 and 15 nucleotides or more in length. Primers and probes cart also be at least 20 nucleotides or more in length, or at least 25 nucleotides or more, or at least 30 nucleotides or more in length. Such primers and probes hybridize specifically to a target sequence under high stringency hybridization conditions. Primers and probes according to the present invention may have complete sequence complementarity with the target sequence, although probes differing from the target sequence and which retain the ability to hybridize to target sequences may be designed by conventional methods.

As used heroin, the "repeatability standard deviation $(RSD_r)$" is the standard deviation of test results obtained under repeatability conditions. "Repeatability conditions" are conditions where test results are obtained with the same method, on identical test items, in the same laboratory, by the same operator, using the same equipment within short intervals of time.

As used herein, the "reproducibility standard deviation $(RSD_R)$" is the standard deviation of test results obtained under reproducibility conditions. Reproducibility conditions are conditions where test results are obtained with the same method, on identical test items, in different laboratories, with different operators, using different equipment. Reproducibility standard deviation describes the inter-laboratory variation.

"Robustness" of a method is a measure of its capacity to remain unaffected by small, but deliberate deviations from the experimental conditions described in the procedure.

"Specificity" of a method refers to the property of the method to respond exclusively to the characteristic or analyte of interest. For example, the specificity of the PCR method described in Example 1, which uses the primers disclosed in SEQ ID NO: 1 and SEQ ID NO: 2, detects Bt11 DNA exclusively.

The "trueness" of a method is the closeness of agreement between the average value obtained from a large series of test results and an accepted reference value. The measure of trueness is typically expressed in terms of percent bias. A method of the invention has a trueness of ±5% across the entire dynamic range.

As used herein, the term "unique" to Bt11 means distinctively characteristic of or diagnostic for event Bt11. Therefore, nucleic acids unique to event Bt11 are not found in other non-Bt11 corn plants.

This invention relates to compositions and improved methods for the quantitative detection of Bt11-specific DNA in biological samples relative to an endogenous maize adh1 gene. Such quantification of Bt11 DNA in, for example a mixture of corn grain comprising Bt11 and non-Bt11 grain, is based on a primer pair and probe designed to detect the 5' Junction sequence in Bt11.

In one embodiment, the present invention encompasses a method of quantifying event Bt11 DNA in a biological sample comprising corn nucleic acids, the method comprising (a) contacting the biological sample with a first pair of primers, comprising a first primer consisting of SEQ ID NO:1 and a second primer consisting of SEQ ID NO: 2, and a fluorescent dye labeled probe comprising SEQ ID NO: 3, wherein the first pair of primers, when used in a nucleic-acid amplification reaction with genomic. DNA from event Bt11 corn produce a first amplicon comprising SEQ ID NO: 4, and wherein the first amplicon is diagnostic for event Bt11; (b) contacting the biological sample with a second pair of primers, comprising a first primer consisting of SEQ ID NO: 5 and a second primer consisting of SEQ ID NO: 6, and a second fluorescent dye labeled probe comprising SEQ ID NO: 7, wherein the second pair of primers, when used in a nucleic-acid amplification reaction with corn genomic DNA, produce a second amplicon comprising SEQ ID NO: 8, and wherein the second amplicon is indicative of the presence of a maize adh1 gene, (c) providing a nucleic acid amplification reaction condition and a PCR instrument capable of performing a quantitative real-time PCR; (d) performing the quantitative real-time PCR using the primers and probes of (a) and (b), thereby producing the first amplicon and the second amplicon; (e) detecting simultaneously the first amplicon and the second amplicon as they are produced by the PCR instrument, and (f) calculating, a relative amount of the first amplicon compared to the second amplicon, whereby the amount of the first amplicon is indicative of the quantity of Bt11 DNA in the biological sample.

In one aspect of this embodiment, the method has a limit of quantification (LOQ) of less than or equal to 0.08% Bt11 DNA concentration.

In another aspect of this embodiment, the method has a limit of detection (LOD) of less than or equal to 0.04% Bt11 DNA concentration.

In yet another aspect of this embodiment, the method has a mean coefficient of linearity ($R^2$) of at least 0.99.

In still another aspect of this embodiment, the method has a relative reproducibility standard deviation ($RSD_R$) of 24% or less at a Bt11 DNA concentration of 0.090%.

In another aspect of this embodiment, the method has a relative repeatability standard deviation ($RSD_r$) of 17% or less at a Bt11 DNA concentration of 0.090%.

In yet another aspect of this embodiment, the method has a trueness value of ±5% or less across the entire dynamic range.

In another embodiment, the present invention encompasses a pair of primers comprising a first primer consisting of SEQ ID NO: 1 and a second primer consisting of SEQ ID NO: 2 which function together in a PCR in the presence of a corn event Bt11 DNA template in a biological sample to produce an amplicon diagnostic for the corn event Bt11.

In one aspect of this embodiment, the amplicon comprises SEQ ID NO: 4.

In yet another embodiment, the present invention encompasses a fluorescent dye labeled probe comprising SEQ ID NO: 3.

The following examples are intended solely to illustrate one or more preferred embodiments of the invention and are not to be construed as limiting the scope of the invention.

EXAMPLES

Example 1

Bt11 Quantitative RT-qPCR Method Development

This Example describes an improved Bt11-specific real-time quantitative PCR (RT-qPCR) method for the determination of the relative amount of event Bt11 DNA to total maize DNA in a biological sample.

The TaqMane® (Applied Biosystems, Foster City, Calif.) assay is a RT-qPCR detection technique in which the accumulation of PCR product is monitored directly during the progress of the PCR reaction. Degradation of target-specific probe molecules by the 5' to 3' exonuclease activity of Taq DNA polymerase during each cycle of amplification produces an accumulation of fluorescence. Increased levels of fluorescence are directly related to the accumulation of PCR product and are detected during each cycle of amplification through the use of a specialized PCR machine, for example, without limitation, ABI PRISM™ 770 or ABI PRISM™ 7900 HT (Applied Biosystems, Foster City. CA).

Cycle thresholds (Ct) are assigned automatically by the PCR instrument to each sample according to the cycle at which the fluorescence exceeds a specific level above background. Samples with higher levels of template at the beginning of the reaction will amplify to detectable levels more quickly and yield lower Ct. For quantification of the amount of event Bt11 DNA in a test sample, the normalized ΔCt values of calibration samples are used to calculate, by linear regression, a reference curve ΔCt-formula. The normalized ΔCt values of the unknown samples are then measured and by means of the calculated regression formula the relative amount of Bt11 event DNA in the unknown sample is estimated. The TaqMan® assay described herein can be used to accurately quantify the level of Bt11 DNA relative to an endogenous calibrator maize gene. Because the endogenous calibrator sequence remains constant relative to total maize genomic DNA, any variation in the relative level of Bt11-specific DNA to the endogenous gene is indicative of a difference in copy number.

1.1 Event-Specific PCR System for Event Bt11 Maize

PCR systems derived from both junction regions between the insert and the genomic DNA of Event Bt11 were tested based on sequence information about the DNA insert and its flanking 5' and 3' border sequences. Assisted by oligonucleotide design software (Primer Express™ V2.0) three probes and six amplification primers were designed for the 5' border and one probe and three amplification primers were designed for the 3' border. Subsequently all possible combinations of these primers and probes were tested experimentally.

Comparison of the Ct values, the ΔRn values, shapes of the amplification plots and the PCR efficiencies led to one primer pair/probe combination which was chosen for further optimization.

The optimal primer pair and probe are located at the 5' genome-insert junction, which produced better results than the 3' junction primers. The forward primer is located in the genomic DNA, the binding site for of the reverse primer is located within the Event Bt11 insert, whereas the probe spans the 5' genome-insert junction. For the specific detection of event Bt11 DNA, a 68-bp nucleic acid fragment overlapping the heterologous insert: DNA and the maize genomic DNA flanking the 5' end of the insert is amplified using the following primers:

```
                                         (SEQ ID NO: 1)
Bt11-ev-f1:  5'-TGTGTGGCCATTTATCATCGA-3'

(SEQ ID NO: 2)
Bt11-ev-r5:  5'-CGCTCAGTGGAACGAAAACTC-3'.
```

PCR products are measured at each cycle (real-time) by means of the following target-specific oligonucleotide probe: Bt11-ev-p1: 5'TTCCATGACCAAAATCCCTTAACGT-GAGT-3' (SEQ ID NO: 3) labeled with a reporter dye, fluorescein (FAM), at its 5' end and a quencher dye, tetramethylrhodamine (TAMRA) at its 3' end.

Using these primers in a reaction with Bt11 maize DNA as the template produces an amplicon comprising SEQ ID NO: 4, which is unique to and diagnostic for event Bt11.

1.2 Maize-Specific Reference PCR System (Adh1)

For the relative quantification of event Bt11 DNA, a pre-existing maize-specific reference PCR system (Hernandez et al. 2004. J. Agric. Food Chem. 52:4632-4637) which amplifies a 135-bp fragment of the maize endogenous alcohol dehydrogenase 1 gene (adh1) (Genbank accession no. AY691949) was used as a reference system for the specific detection of sequences of Zea mays. This reference system uses the following primers:

```
                                         (SEQ ID NO: 5)
Zmadh1-F:  5'-CGTCGTTTCCCATCTCTTCCT-3'

(SEQ ID NO: 6)
Zmadh1-R:  5'-CCACTCCGAGACCCTCAGTC-3'
```

PCR products are measured at each cycle (real-time) by means of the following target-specific oligonucleotide probe: Zmadh1-P: 5'-AATCAGGGCTCATTTTCTCGCTCCTCA-3' (SEQ ID NO: 7) labeled with VIC™ (Applied Biosystems, Foster City, Calif.) dye at the 5' end and TAMRA at the 3' end.

Using these primers in a reaction with maize DNA as the template produces an amplicon comprising SEQ ID NO: 8, which is indicative of the presence of maize adh1.

1.1 Calculation of Calibration Curve

The calibration curve consists of five samples containing fixed percentages of Bt11 DNA in a total amount of 250 ng maize DNA. The concentration of Bt11 DNA in the standard samples ranged from 10% to 0.08%. A calibration curve is produced by plotting the ΔCt values of calibration samples against the logarithm of the respective Bt11% concentration; the slope (a) and the intercept (b) of the calibration curve (y=ax+b) are then used to calculate the mean Bt11% content of the blind samples based on their normalized ΔCt values.

During the TaqMan™ reaction, the software accompanying the ABI PRISM™ 7900 HT instrument detects the accumulation of PCR product by the accumulation of fluorescence. Normalized fluorescence relative to established baseline levels (ΔRn) is plotted versus cycle number. A Ct value is obtained by drawing an arbitrary cutoff through the reactions so that the line passes through the log phase of each reaction. The sequence detection system software with the ABI PRISM™ 7900 HT instrument provides the cycle number at which the accumulation of fluorescence (PCR product) of a particular reaction crosses the threshold (Ct) The FAM Ct(Bt11) value is compared to the VIC Ct (adh1) value to normalize the FAM Ct value of each reaction to the level of total nucleic acids present to yield ΔCt[ΔCt=Ct(FAM)–Ct (VIC)]. This calculation removes any variation contributed by unequal template input in reactions. Because the number of copies of endogenous maize gene per genome remains constant, a change in ΔCt corresponds to a change in quantity for copy) of the Bt11 DNA. By comparing the ΔC value of the unknown samples to the ΔCt of a known control, ΔΔCt is obtained [ΔΔCt=ΔCt(unknown)−ΔCt (Known)]. Copy number can then be calculated using the ΔΔCt value using the equation: Copy Number=$2^{\Delta\Delta Ct}$.

1.2 Real-Time PCR Set-Up

PCRs are carried out in 96-well reaction plates. The procedure is a simplex system, in which the calibrator maize adh1 endogenous assay and the target Bt11 assay are simultaneously performed in separate wells. In two reaction cubes, one for the Bt11 system and one for the adh1 system, on ice, add the components (except DNA) in Tables 1 and 2 in the order listed to prepare the master mixes. The 2X Sigma Jumpstart Ready Mix is supplemented with 550 µl of 1M $MgCl_2$ and 20 µl of 10000× sulfothodamine 101. Mix gently and centrifuge briefly. Prepare two more reaction tubes, one for Bt11 and one for adh1 master mixes, for standard curve DNA samples, unknown DNA samples and control DNA samples. Add to each reaction tube the correct amount of master mix (e.g. 20×3=60 µl master mix for three PCR repetitions). Add to each tube the correct amount of DNA shown in Tables 1 and 2 (e.g. 5×3=15 µl DNA for three PCR repetitions).

TABLE 1

Amplification reaction mixture in the final volume/concentration per reaction well for the maize adh1 reference system.

| Component | Final concentration | µL/reaction |
| --- | --- | --- |
| Sigma Jumpstart ReadyMix (2x) | 1x | 12.5 |
| Zm adh1- F primer (10 µM) | 300 nM | 0.75 |
| Zm adh1- R primer (10 µM) | 300 nM | 0.75 |
| Zm adh1- P probe (10 µM) | 200 nM | 0.50 |
| Nuclease free water | # | 5.50 |
| Template DNA (max 250 ng) | # | 5 |
| Total reaction volume: | | 25 |

TABLE 2

Amplification reaction mixture in the final volume/concentration per reaction well for the Bt11-specific system.

| Component | Final concentration | µL/reaction |
| --- | --- | --- |
| Sigma Jumpstart ReadyMix (2x) | 1x | 12.5 |
| Bt11-ev-f1 primer (10 µM) | 200 nM | 0.50 |
| Bt11-ev-r5 primer (10 µM) | 200 nM | 0.50 |
| Bt11-ev-p1 probe (10 µM) | 150 nM | 0.38 |
| Nuclease free water | # | 6.12 |
| Template DNA (max 250 ng) | # | 5 |
| Total reaction volume: | | 25 |

Vortex each tube for approximately 10 seconds to help reduce the variability among repetitions of each sample. Spin down the tubes in a microfuge. Aliquot 25 µl in each PCR reaction well. Seal the reaction plate with an optical cover or optical caps. Centrifuge the plate at approximately 250×g for approximately 1 minute at a range from 4° C. to approximately room temperature. Place the plate in the PCR instrument and run the PCR with cycling conditions described in Table 3.

TABLE 3

Cycling program for maize Bt11/adh1 systems.

| Step | Stage | T° C. | Time (Sec) | Acquisition | Cycles |
| --- | --- | --- | --- | --- | --- |
| 1 | UNG | 50° C. | 120 | No | 1 |
| 2 | Initial denaturation | 95° C. | 600 | No | 1 |
| 3 | Denaturation | 95° C. | 15 | No | 40 |
|   | Aneealing & Extension | 60° C. | 60 | Yes | |

After running the real-time PCR protocol described above, the results are analyzed by the following procedure:

To set the threshold, display the amplification curves of one system (e.g. Bt11) in logarithmic mode. Locate the threshold line in the area of the curve where the amplification profiles are parallel (exponential phase of pCR). Update Ct values as required. Switch to the linear mode by clicking on the Y axis of the amplification plot, and cheek that the threshold previously set falls within the geometric phase of the curves.

To set the baseline, determine the cycle number at which the threshold line crosses the first amplification curve and set the baseline three cycles before that value (e.g. earliest Ct=25, set the baseline crossing at Ct=25−3=22).

Repeat the procedure described above on the amplification plots of the other system (e.g. adh1 system).

After having defined a threshold value within the logarithmic phase of amplification as described above, the instrument's software calculates the Ct-values for each reaction. The reference Ct-curve is generated by plotting the Ct-values measured for the calibration points against the logarithm of the Bt11% content, and by fitting a linear regression line into these data. Thereafter, the regression formula is used to estimate the relative amount of Bt11 DNA in the unknown DNA samples.

The specificity of the Bt11 assay (forward/reverse primers and probe) was experimentally tested in real-time PCR against DNA extracted from samples containing transgenic maize known in the art including Bt11, Bt10, NK603, MON810, MON863, MON810×MON863, TC1507, MIR604, Bt176, GA21, MON88017, T25 and Herculex® RW (DAS-59122-7).

The results demonstrate that none of the above mentioned transgenic corn lines tested, except the positive control Bt11, produced amplicons in replicated samples when 100 ng total DNA per reaction were used.

Example 2

Validation of Bt11 Quantitative RT-qPCR Method

The method described in Example 1 is optimized for quantification of Bt11 DNA in biological samples from mixtures of Bt11 and conventional maize seeds. The method exploits a unique DNA sequence in the region between the insert and the plant genome. The sequence is specific: to event Bt11 corn and thus imparts even specificity to the method.

2.1 Precision/Accuracy/Dynamic Range/LOQ/LOD in order to determine precision, accuracy, dynamic range. LOQ and LOD the following experimental design was carried out in eight independent runs.

The calibration samples (Std1 to Std6) were produced by preparing solutions of 50 ng/µl (250 ngreaction) of total genomic DNA with 100%; 10%; 5%; 1%; 0.5% and 0.1% Event Bt11 DNA in non-transgenic maize DNA background.

The dilution scheme of the Bt11 standard and the corresponding total genomic DNA content in the PCR reaction is shown in Table 4.

TABLE 4

Dilution scheme of the calibration samples.

| | Amount in each standard (ng) | | | | | |
|---|---|---|---|---|---|---|
| Sample Code | Std1 | Std2 | Std3 | Std4 | Std5 | Std6 |
| Total DNA content in PCR | 250 | 250 | 250 | 250 | 250 | 250 |
| Total Bt11 DNA content in PCR | 250 | 25 | 12.5 | 2.5 | 1.25 | 0.25 |

A calibration curve was produced by plotting mean ACT values of calibration samples against the logarithm of the respective Bt11% contents; the slope (a) and the intercept (b) of the calibration curve (y=ax+b) were then used to calculate the mean % Bt11 content of the reference samples based on their normalized ACT values.

Three negative controls (NTC) per system were run to verify purity of reagents. Each reference sample (containing, different ratios of Event Bt11 DNA in non-transgenic maize DNA background) was analyzed at 250 ng genomic DNA per reaction in triplicate.

Data analysis has been accomplished by using baseline setting 3-19 for the Adh1 system and 3-21 for the Event Bt11-specific detection system. The threshold values were 0.4 (Adh1) and 0.7 (Bt11) on the ABI 7900 HT detection system.

For each of the 5 samples (ranging from 5.0% down to 0.08% Event Bt11 DNA in non-transgenic maize DNA), the mean value (MEAN), the relative deviation from the expected value (BIAS) as well as the standard deviation (STDEV) and the relative standard deviation ($RSD_r$) of the quantification results were calculated in order to determine accuracy and repeatability. The results are shown in Table 5.

TABLE 5

Quantification results of 8 independent PCR runs under repeatability conditions for Event Bt11.

| Bt11-Level | Mean | Bias | Stdev | $RSD_r$ |
|---|---|---|---|---|
| 5.0% | 5.4% | 8.0% | 0.32% | 5.9% |
| 2.0% | 1.9% | −5.0% | 0.18% | 9.5% |
| 0.90% | 0.90% | 0.0% | 0.070% | 7.8% |
| 0.50% | 0.53% | 6.0% | 0.076% | 14.3% |
| 0.080%[a] | 0.068% | −15.0% | 0.0111% | 16.3% |
| 0.040%[b] | | All positive | | |

[a] Limit of quantification (LOQ)
[b] Limit of detection (LOD)

The relative deviation of the mean value from the expected (true) value ranged between −13.8% and 0% over the entire dynamic range.

Precision (Repeatability standard deviation $RSD_r$) values for all samples between 5.0% and 0.08% Bt11 concentration ranged front 5.9% to 16.3% relative standard deviation.

The relative limit of detection (LOD) of the method was determined to be less than or equal to 0.04% in 250 ng of total maize DNA.

The relative limit of quantification (LOQ) of the method is less than or equal to 0.08% in 250 ng of total maize DNA.

2.2 Amplification Efficiency and $R^2$ Coefficient

In order to access amplification efficiency (E) and $R^2$ coefficient of the Event Bt11-specific (single) PCR system linear regression analysis of Event Bt11 Ct values versus log[% Bt11-content] was performed. The regression lines of the standards of 8 independent runs (see 2.1 above) were evaluated and the regression parameters including slope, intercept and $R^2$ were determined. The efficiency of the amplification was calculated by the following equation: $E=[10^{(-1/slope)}]-1$. Results are shown M Table 6.

TABLE 6

Regression parameters and PCR efficiencies of the Event Bt11-specific regression lines

| | Slope | Intercept | $R^2$ | E |
|---|---|---|---|---|
| Run1 | −3.48 | 31.7 | 1.000 | 0.94 |
| Run2 | −3.61 | 31.9 | 0.999 | 0.89 |
| Run3 | −3.48 | 31.7 | 0.999 | 0.94 |
| Run4 | −3.53 | 31.8 | 0.999 | 0.92 |
| Run5 | −3.51 | 31.7 | 0.999 | 0.93 |
| Run6 | −3.40 | 31.5 | 1.000 | 0.97 |
| Run7 | −3.57 | 31.6 | 0.999 | 0.90 |
| Run8 | −3.55 | 31.5 | 1.000 | 0.91 |
| MEAN | −3.52 | 31.7 | 0.999 | 0.93 |

In order to assess amplification efficiency E and $R^2$ coefficient of the ΔCt based Event Bt11 detection method linear regression analysis of ΔCt values versus log[% Bt11-content] was performed. The regression lines of the standards of 8 independent runs (see 4.3) were evaluated and the regression parameters including slope, intercept and $R^2$ have been determined. The efficiency of the amplification was calculated by the following equation: $E=[10^{(-1/slope)}]-1$. Results are shown in Table 7.

TABLE 7

Regression parameters and PCR efficiencies of the calibration curves based on ΔCt values of the calibration samples.

| | Slope | Intercept | $R^2$ | E |
|---|---|---|---|---|
| Run1 | −3.43 | 9.2 | 1.000 | 0.96 |
| Run2 | −3.55 | 9.3 | 0.999 | 0.91 |
| Run3 | −3.42 | 9.2 | 0.999 | 0.96 |
| Run4 | −3.45 | 9.2 | 0.999 | 0.95 |
| Run5 | −3.46 | 9.5 | 0.999 | 0.95 |
| Run6 | −3.34 | 9.4 | 0.998 | 0.99 |
| Run7 | −3.50 | 9.5 | 1.000 | 0.93 |
| Run8 | −3.50 | 9.4 | 0.999 | 0.93 |
| MEAN | −3.46 | 9.3 | 0.999 | 0.95 |

In order to assess the robustness of the method PCR reactions were carried out under variable concentrations of master mix and annealing temperatures.

The stability of both detection systems concerning changes in the concentration of major reaction components an experiment was conducted at +20% and at −20% of the concentration of the master mix. Three samples (0.080%, 0.90% and 5.0% of Event Bt11 DNA in non-transgenic maize. DNA) were analyzed at 250 ng genomic DNA per reaction. The mean of triplicates is shown in Table 8.

TABLE 8

Quantification results at +/−20% of master mix

| | Expected (true) value (% Bt11) | | |
|---|---|---|---|
| | 0.080% | 0.90% | 5.0% |
| Master Mix +20% | | | |
| Quantification results | 0.056% | 0.74% | 4.7% |
| Relative deviation from true | −30.0% | −17.8% | −6.0% |

TABLE 8-continued

Quantification results at +/−20% of master mix

| | Expected (true) value (% Bt11) | | |
|---|---|---|---|
| | 0.080% | 0.90% | 5.0% |
| Master Mix −20% | | | |
| Quantification results | 0.060%[a] | 0.74% | 5.3% |
| Relative deviation from true | −25.0% | −17.8% | 6.0% |

[a]One outlier excluded

In order to assess the influence of varying the annealing temperature three samples (0.080%, 0.90% and 5.0% of Event Bt11 DNA in non-GM maize DNA background) were analyzed at 250 ng genomic DNA per reaction with annealing temperatures of 58° C. and 62° C. on the ABI 7900 HT sequence detection system. Results are shown in Table 9.

TABLE 9

Quantification results using different annealing temperatures.

| | Expected (true) value (% Bt11) | | |
|---|---|---|---|
| | 0.080% | 0.90% | 5.0% |
| 58° C. | | | |
| Quantification result 1 | 0.057% | 1.09% | 5.9% |
| Relative deviation from true | −28.8% | 21.0% | 18.0% |
| Quantification result 2 | 0.060% | 0.90% | 5.5% |
| Relative deviation from true | −25% | 0.0% | 10.0% |
| 62° C. | | | |
| Quantification result 1 | 0.071% | 0.89% | 5.2% |
| Relative deviation from true | −11.3% | −1.1% | 4.0% |
| Quantification result 2 | 0.056% | 0.93% | 5.6% |
| Relative deviation from true | −30.0% | 3.3% | 12.0% |

In order to assess the influence of different real-time PCR platforms, three samples (0.080%, 0.90% and 5.0% Event Bt11 DNA in non-GM maize DNA background) were analyzed at 250 ng genomic DNA per reaction each on ABI PRISM® 7700, 7500 fast (run in non-fast mode) and Stratagene Mx 3005P detection system. The two quantification results obtained for each sample are shown in Table 10.

TABLE 10

Quantification results using different platforms.

| | Expected (true) value (% Bt11) | | |
|---|---|---|---|
| | 0.080% | 0.90% | 5.0% |
| ABI 7500 fast | | | |
| Quantification result 1 | 0.077% | 0.82% | 5.7% |
| Relative deviation from true | −3.75% | −8.9% | 14.0% |
| Quantification result 2 | 0.072% | 0.85% | 5.6% |
| Relative deviation from true | −10.0% | −5.6% | 12.0% |
| ABI PRISM ® 770 | | | |
| Quantification result 1 | 0.082% | 0.85% | 5.9% |
| Relative deviation from true | 2.5% | −5.5% | 18.0% |
| Quantification result 2 | 0.058% | 0.92% | 4.8% |
| Relative deviation from true | −27.5% | 2.2% | −4.0% |
| Stratagene Mx 3005P | | | |
| Quantification result 1 | 0.057% | 1.09% | 4.7% |
| Relative deviation from true | −28.8% | 21.1% | −6.0% |
| Quantification result 2 | 0.083% | 0.81% | 4.0% |
| Relative deviation from true | 3.8% | −10.0% | −20.0% |

In order to assess the test results under reproducibility conditions two quantification runs were performed at two different laboratories, Lab 1 and Lab 2. Different samples containing 0.08%-5.0% Bt11 DNA concentration were analyzed (each in triplicate) at 250 ng genomic DNA per reaction on different sequence detection systems. Table 11 shows the two quantification results obtained for each concentration of Bt11 DNA at each laboratory. The reproducibility standard deviation ($RSD_R$) was calculated to be approximately 9.0% at the 0.08% Bt11 concentration.

TABLE 11

Quantification results under reproducibility conditions (inter-laboratory).

| | 0.080% | 0.50% | 0.90% | 2.0% | 5.0% |
|---|---|---|---|---|---|
| Lab 1 (ABI PRISM 7900 HT) | | | | | |
| Quantification result 1 | 0.068% | 0.49% | 0.96% | 2.1% | 4.6% |
| Relative deviation from true | −15.0% | −2.0% | 6.7% | 5.0% | −8.0% |
| Quantification result 2 | 0.080% | 0.57% | 0.88% | 2.1% | 4.7% |
| Relative deviation from true | 0% | 14.0% | −2.2% | 5.0% | −6.0% |
| Lab 2 (ABI PRISM 7700) | | | | | |
| Quantification result 1 | 0.076% | 0.49% | 0.96% | 2.0% | 5.0% |
| Relative deviation from true | −5.0% | −2.0% | 6.7% | 0% | 0% |
| Quantification result 2 | 0.065% | 0.51% | 1.14% | 2.3% | 5.9% |
| Relative deviation from true | −18.8% | 2.0% | 26.7% | 15.0% | 18.0% |

The quantification method described herein was submitted to the European Commission Joint Research Centre JRC, Biotechnology and GMOs Unit of the institute for Health and Consumer Protection) as Community Reference Laboratory for Genetically Modified Food and Feed (CRL-GMFF). The JRC organized an international collaborative study involving 12 laboratories. Each laboratory tested five concentrations of Bt11 DNA including 0.09%, 0.40%, 0.90%, 5.00% and 8.00%. The results of this multi-laboratory validation study were published in CRL publication CRLVL10/07VR (2008), which is available on the World Wide Web at gmo-crl.jrc.e-c.europa.eu/. The method had a mean coefficient of linearity ($R^2$) of 0.99, a $RSD_r$ of 17% at the 0.09% Bt11 concentration, a $RSD_R$ of 24% at the 0.09% Bt11 concentration and the highest value of bias (trueness) of −5% at the 5% Bt11 concentration.

Example 3

Assessment of Prior Method

Other event Bt11 quantitation assays have been published (Ronning et al. 2003. Eur. Food Res. Technol. 216:347-354 and European Commission JRC Community Reference Laboratory (CRL) published 2004, located on the world wide web at gmo-crl.jrc.it//summaries/Bt11-protocol.pdf, which is based on the Ronning et al. method).

To assess this quantification method, PCR assays were performed by an independent laboratory on mixtures of Bt11 DNA and non-transgenic DNA as described in the CRL publication referenced above. This assay uses primers and probes designed to bind to the 3' genome-insert region. Results of multiple experiments suggest that PCR efficiency of the Bt11 reactions using this method is inadequate. Slopes of Bt11 standard regression lines suggest a lack of PCR efficiency, as compared to the adh1 standard regression lines. In 5 out of 6 experiments, correlation of Bt11 standard reactions was poorer than for adh1 standard reactions when DNA solutions used for Bt11 and adh1 standard series were identical. Results further suggest that the previous method may have deficiencies in precision, repeatability and robustness as well.

All publications and published patent documents cited in this specification are incorporated herein by reference to the same extent as if each individual publication or patent document was specifically and individually indicated to be incorporated by reference.

What is claimed is:

1. A method of quantifying event Bt11 DNA in a biological sample comprising corn nucleic acids, the method comprising:
   (a) contacting said biological sample with a first pair of primers, comprising a first primer consisting of SEQ ID NO: 1 and a second primer consisting of SEQ ID NO: 2, and a fluorescent dye labeled probe comprising SEQ ID NO: 3, wherein said first pair of primers, when used in a nucleic-acid amplification reaction with genomic DNA from event Bt11 corn, produce a first amplicon comprising SEQ ID NO: 4, and wherein said first amplicon is diagnostic for event Bt11;
   (b) contacting said biological sample with a second pair of primers, comprising a first primer consisting of SEQ ID NO: 5 and a second primer consisting of SEQ ID NO: 6, and a second fluorescent dye labeled probe comprising SEQ ID NO: 7, wherein said second pair of primers, when used in a nucleic-acid amplification reaction with corn genomic DNA, produce a second amplicon comprising SEQ ID NO: 8, and wherein said second amplicon is indicative of the presence of a maize adh1 gene;
   (c) providing a nucleic acid amplification reaction condition and a PCR instrument capable of performing a quantitative real-time PCR;
   (d) performing the quantitative real-time PCR using the primers and probes of (a) and (b), thereby producing said first amplicon and said second amplicon;
   (e) detecting simultaneously said first amplicon and said second amplicon as they are produced by said PCR instrument; and
   (f) calculating a relative amount of said first amplicon compared to said second amplicon, whereby the amount of said first amplicon is indicative of the quantity of Bt11 DNA in said biological sample.

2. The method of claim 1, wherein said method has a limit of quantification (LOQ) of less than or equal to 0.08% Bt11 DNA concentration.

3. The method of claim 1, wherein said method has a limit of detection (LOD) of less than or equal to 0.04% Bt11 DNA concentration.

4. The method of claim 1, wherein said method has a mean coefficient of linearity ($R^2$) of at least 0.99.

5. The method of claim 1, wherein said method has a relative reproducibility standard deviation ($RSD_R$) of 24% or less at a Bt11 DNA concentration of 0.090%.

6. The method of claim 1, wherein said method has a relative repeatability standard deviation ($RSD_r$) of 17% or less at a Bt11 DNA concentration of 0.090%.

7. The method of claim 1, wherein said method has a trueness value of ±5% or less across the entire dynamic range.

* * * * *